United States Patent [19]

Ito et al.

[11] Patent Number: 5,239,185
[45] Date of Patent: Aug. 24, 1993

[54] METHOD AND EQUIPMENT FOR MEASURING ABSORPTANCE OF LIGHT SCATTERING MATERIALS USING PLURAL WAVELENGTHS OF LIGHT

[75] Inventors: Yoshitoshi Ito, Ome; Fumio Kawaguchi; Minoru Yoshida, both of Tokyo; Keiichi Nagai, Higashiyamato; Hiroyuki Kohida, Fuchu, all of Japan

[73] Assignee: Hitachi, Ltd., Tokyo, Japan

[21] Appl. No.: 902,493

[22] Filed: Jun. 23, 1992

Related U.S. Application Data

[63] Continuation of Ser. No. 717,481, Jun. 19, 1991, abandoned.

[30] Foreign Application Priority Data

Jun. 22, 1990 [JP] Japan .................... 2-162651

[51] Int. Cl.$^5$ .................... G01N 15/06; G01N 33/16
[52] U.S. Cl. .................... 250/573; 250/226; 356/39
[58] Field of Search .................... 250/226, 339, 573, 574, 250/343; 356/39, 40, 41, 432, 442, 341; 128/633

[56] References Cited

U.S. PATENT DOCUMENTS

| | | | |
|---|---|---|---|
| 4,350,441 | 9/1982 | Wicnienski | 356/40 |
| 4,714,341 | 12/1987 | Hamaguri et al. | 356/41 |
| 4,730,112 | 3/1988 | Wong | 250/343 |
| 4,805,623 | 2/1989 | Jöbsis | 356/41 |
| 4,819,752 | 4/1989 | Zelin | 356/41 |
| 4,824,242 | 4/1989 | Frick et al. | 356/41 |
| 4,863,265 | 9/1989 | Flower et al. | 356/41 |
| 4,997,769 | 3/1991 | Lundsgaard | 356/39 |
| 5,015,099 | 5/1991 | Nagai et al. | 250/339 |

FOREIGN PATENT DOCUMENTS

| | | |
|---|---|---|
| 210417 | 2/1987 | European Pat. Off. |
| 240742 | 10/1987 | European Pat. Off. |
| 265952 | 5/1988 | European Pat. Off. |

OTHER PUBLICATIONS

Quantitative analysis of hemoglobin oxygenation state of rate brain in situ by near-infrared spectrophotometry (O. Hazeki et al, American Physiological Society, 1988, pp. 796-802).

Noninvasive technique for oximetry of blood in retinal vessels, Applied Optics, 15 Mar. 1988, vol. 27, No. 6, pp. 1113-1125.

Primary Examiner—David C. Nelms
Assistant Examiner—John R. Lee
Attorney, Agent, or Firm—Fay, Sharpe, Beall, Fagan, Minnich & McKee

[57] ABSTRACT

In order to make it possible to measure the light absorption coefficient of various sorts of substances contained in a light scattering material with a high precision, the wavelength of light transmitted through the light scattering material is varied and the coefficient of light absorption is calculated, starting from a ratio of variations in the intensity of the transmitted light to variations in the wavelength.

14 Claims, 5 Drawing Sheets

F I G. 2A
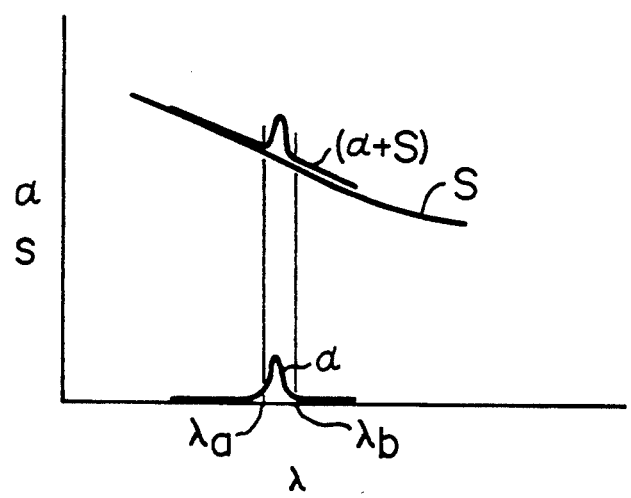
F I G. 2B
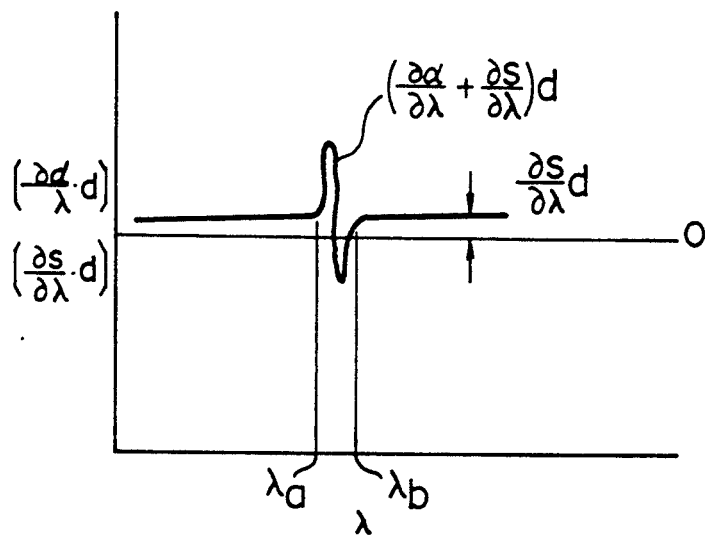
F I G. 2C
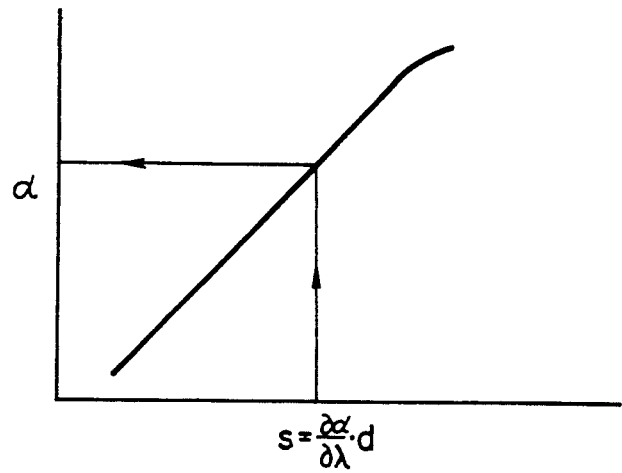

F I G. 3
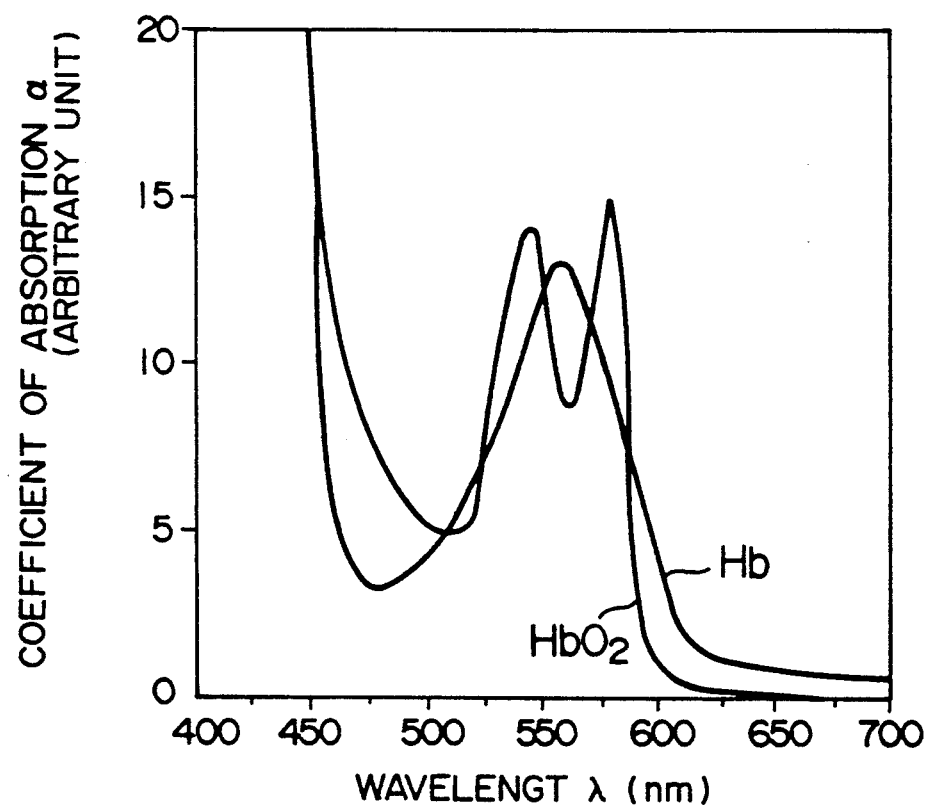

METHOD AND EQUIPMENT FOR MEASURING ABSORPTANCE OF LIGHT SCATTERING MATERIALS USING PLURAL WAVELENGTHS OF LIGHT

This application is a continuation of application Ser. No. 07/717,481, filed Jun. 19, 1991 now abandoned.

BACKGROUND OF THE INVENTION

The present invention relates to a method and an apparatus for measuring a coefficient of light absorption of substances contained in light scattering materials.

When light is injected in a transparent material, the intensity I of transmitted light is given by the following expression:

$$I = I_0 \exp-\{\alpha d\} \quad (1)$$

where $I_0$ represents the intensity of incident light injected in the transparent material; $\alpha$ the coefficient of absorption representing the rate of decrease of light due to light absorption per unit thickness of the material; and d the thickness of the material (optical path length). Consequently, such a coefficient of light absorption $\alpha$ of the transparent material can be obtained, starting from a value obtained by measuring the intensity of light, which has been transmitted through the material, using Eq. (1).

However, for a material having a light-scattering property, light transmitted through the light scattering material is subjected to attenuation due to light scattering, besides attenuation due to light absorption. That is, the intensity I of light, which has been transmitted through the light scattering material, is given by a following expression:

$$I = I_0 \exp-\{\alpha d + sd\} \quad (2)$$

where s is a coefficient of light scattering representing the rate of decrease of light due to light scattering per unit thickness of the material.

As can be understood from Eq. (2), since the intensity of light transmitted through the light scattering material varies, depending also on the value of the coefficient of light scattering s, it is not possible to obtain the coefficient of light absorption $\alpha$, starting only from one measured value of the transmitted light. Therefore, heretofore, apart from the intensity $I_1$ of the transmitted light for one wavelength, for which the coefficient of light absorption $\alpha$ is unknown, the intensity $I_2$ of the transmitted light for another wavelength, for which the coefficient of light absorption $\alpha_0$ is known, is measured and the unknown coefficient of light absorption $\alpha$ is calculated by using these measured values. That is, intensities $I_1$ and $I_2$ of transmitted light for two different wavelengths are measured and the ratio of these two measured values is formed, as indicated by the following expression. The unknown coefficient of light absorption $\alpha$ is obtained by eliminating the coefficient of light scattering s in this way. That is, in the present state of the technique, starting from two measured values:

$$I_1 = I_0 \exp-\{\alpha d + sd\}$$

$$I_2 = I_0 \exp-\{\alpha_0 d + sd\},$$

the ratio of the measured values $$I_1/I_2 = \exp-\{(\alpha - \alpha_0)d\}$$

is formed to obtain the unknown coefficient of light 0 absorption $\alpha$.

In the prior art method described above, it is supposed that the rate of decrease of transmitted light due to light scattering is not varied (equal to each other) for the two wavelengths used for the measurement. However, strictly speaking, this assumption is rarely valid. In particular, in the case where the light scattering power of the material is remarkable, since the value of the coefficient of light scattering s is very great with respect to the value of the coefficient of light absorption $\alpha$, the difference itself in the coefficient of light scattering s between the two wavelengths is often greater than the coefficient of light absorption $\alpha$. For this reason, by the prior art method described above, it was practically difficult to obtain the value of the coefficient of light absorption $\alpha$ with a high precision.

SUMMARY OF THE INVENTION

The present invention removes such a drawback by the prior art method, and the object thereof is to provide an improved measuring method capable of measuring alight absorption coefficient of various sorts of substances contained in light scattering materials, and a measuring equipment for realizing the method.

In order to achieve the above object, by the method according to the present invention the wavelength of light transmitted by the light scattering materials is varied and the coefficient of light absorption is calculated, starting from the rate of the variation in the intensity of transmitted light with respect to the variation in the wavelength.

In more detail, in the method and the equipment of measuring absorptance of alight scattering material, a light scattering material is irradiated alternately with a first and a second laser light beam having slightly different wavelengths within a wavelength region selectively absorbed by the light scattering material; a first ratio of a ratio of an intensity difference between the first and second laser light beams transmitted through the light scattering material to a wavelength difference between the first and second laser light beams to the intensity of the first laser light beam transmitted through the light scattering material, is measured; the light scattering material is irradiated alternately with a third and a fourth laser light beam having slightly different wavelengths outside of the wavelength region selectively absorbed by the light scattering material; a second ratio of a ratio of an intensity difference between the third and fourth laser light beams transmitted through the light scattering material to a wavelength difference between the third and fourth laser light beams to the intensity of the third laser light beam transmitted through the light scattering material, is measured; and a difference between the first ratio and the second ratio is figured out to obtain absorptance of the light scattering material corresponding to the difference.

Attenuation of light due to light scattering, which acts as measurement noise, when the coefficient of absorption is obtained by measuring the intensity of transmitted light, is produced by reflection, diffraction, refraction, etc. of light used for the measurement. In a light scattering material there exist interfaces due to variations in the composition and particles, which are factors of light scattering. The intensity of the light scattering varies, depending on the magnitude of variations in the refraction index at the interfaces described above, direction of the interfaces, shape of the interfaces, size, shape and direction of the particles described above, intensity of light absorption, etc. Further, these factors of light scattering have different wavelength dependencies. In the case where, taking a certain wavelength as a reference, the wavelength is varied in the neighborhood thereof, there are factors of scattering acting so as to increase the amount of transmitted light, and on the contrary there exist also factors of scattering acting so as to decrease it.

Light transmitted through a material is attenuated by light scattering due to such a number of factors. For this reason, the spectrum of transmitted light through the light scattering material due to this light scattering represents synthesized characteristics as a result of integrating various wavelength dependencies of these factors of light scattering existing in the material. Although each of the factors of light scattering has proper wavelength dependence characteristics, these proper characteristics are averaged when they are integrated for different factors. As a result, characteristics having a relatively small ratio of the rate of decrease in the intensity of transmitted light due to light scattering, when the wavelength is varied, can be obtained.

On the other hand, characteristics of light absorption by a light absorbing substance have a shape proper to that substance. This proper shape for to that substance remains unchanged, even if the substance is in a light scattering material. The rate of decrease in the intensity of transmitted light due to the absorption by an optical absorbing material, when the wavelength of light is varied, is proportional to the value of the tangent of an absorption spectrum curve. Consequently, in a wavelength region of the absorption spectrum curve, where there is a light absorption peak, the rates of variations in the rate of decrease in the intensity of transmitted light due to light absorption is very great.

As described above, the rates of variations in the rate of decrease in the intensity of transmitted light with respect to variations in the wavelength differ remarkably from each other in the magnitude thereof for the attenuation due to light scattering and for the attenuation due to light absorption. According to the present invention, light absorption characteristics of a light absorbing substance contained in a light scattering material are measured with a high precision, utilizing this difference.

BRIEF DESCRIPTION OF THE DRAWINGS

FIGS. 2A, 2B and 2C are graphs for explaining characteristics of light absorption and light scattering in a light scattering material;

FIG. 3 shows curves indicating light absorption characteristics of hemoglobin;

DESCRIPTION OF THE PREFERRED EMBODIMENTS

Hereinbelow, before explanation in detail of the embodiments of the present invention, the construction in principle of the method and the equipment for measurement according to the present invention will be explained.

Figure 1:
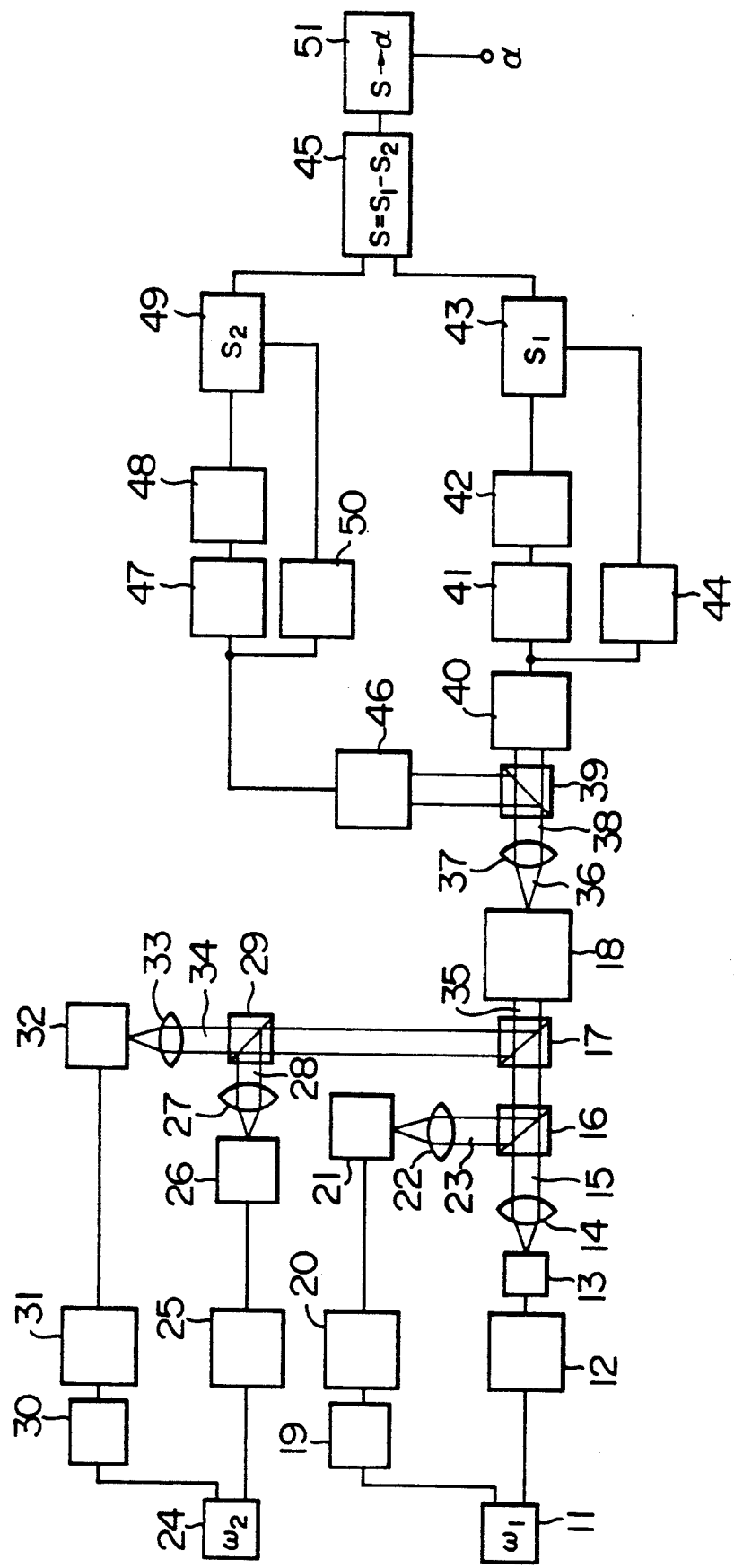
FIG. 1 is a block diagram indicating a fundamental construction of the equipment for measuring the coefficient of light absorption according to the present invention.

FIG. 1 shows a fundamental construction of the equipment for measuring absorptance of light scattering materials according to the present invention. This equipment consists roughly of a light source unit, optical measurement units and a signal processing unit. In the figure, reference numerals 11 to 17 as well as 19 to 35 denote elements constituting the light source unit and 36 to 51 denote elements constituting the optical measurement units and the signal processing unit. Reference numeral 18 represents a sample to be measured.

The light source unit described above is provided with 4 semiconductor laser devices (hereinbelow called laser diodes) 13, 21, 26 and 32, which are activated by separate diode power supplies 12, 20, 25 and 31, respectively. Further clock signal generating circuits 11 and 24 are disposed for controlling these laser diode power supplies to determine the duty cycle of laser light pulses of the different laser diodes. Furthermore there are disposed clock signal inverting circuits 19 and 30 on the input sides of clock signals to the power supplies 20 and 31, respectively, so that clock signals coming from the clock signal generating circuits 11 and 24 are transmitted to the laser diode power supplies 20 and 31, after having been inverted by the inverting circuits 19 and 30, respectively. Since oscillations of the laser diodes 21 and 32 are controlled by these inverted signals, the laser diodes 21 and 32 are oscillated (activated) alternately with respect to the laser diodes 13 and 26, respectively.

It is supposed that the wavelength of laser of the laser diode 21 is selected at a wavelength $\lambda_1 + \Delta\lambda_1$, which is slightly different from the wavelength of laser $\lambda_1$ of the laser diode 13, while the wavelength of laser of the laser diode 32 is selected at a wavelength $\lambda_2 + \Delta\lambda_2$, which is slightly different from the wavelength of laser $\lambda_2$ of the laser diode 26. The laser light beams 15, 23, 28 and 34 outputted by these laser diodes 13, 21, 26 and 32 are guided to one optical path 35 through optical elements such as a polarizer 16, 29, a dichroic mirror 17, etc. after having been transformed into parallel beams by means of collimator lenses 14, 22, 27 and 33, respectively, so that the sample is irradiated therewith.

Here the content of the light transmitted by the sample 18 is as follows. The intensity $I_t$ transmitted by the sample is given as follows, using Eq. (2) described previously;

$$I_t = I_0 \exp\{-(\alpha d + sd)\}$$

Further, differentiating the two members of this equation with respect to the wavelength $\lambda$, a following equation is obtained:

$$-\frac{1}{I_t} \frac{\partial I_t}{\partial \lambda} = d\left(\frac{\partial \alpha}{\partial \lambda} + \frac{\partial s}{\partial \lambda}\right) \tag{3}$$

Eq. (3) expresses that by differentiating the intensity of transmitted light $I_t$ with respect to the wavelength $\lambda$ and multiplying the derivative thus obtained by the inverse of the intensity of transmitted light $I_t$, a value is obtained, which is proportional (proportionality coefficient being d) to the sum of the derivative by wavelength of the absorption coefficient $\alpha$ and the derivative by wavelength of the scattering coefficient s.

FIGS. 2A and 2B are graphs indicating the wavelength dependencies of the absorption coefficient $\alpha$ as well as the scattering coefficient s and the derivative by wavelength, respectively. The curve ($\alpha$) in FIG. 2A represents the absorption coefficient $\alpha$ of the sample material and the curve (s) similarly the scattering coefficient s of the sample material. Consequently the intensity spectrum of the light transmitted by the sample material can be expressed by a curve ($\alpha+s$), for which influences of both the coefficient of absorption $\alpha$ and the coefficient of scattering s are taken into account.

As indicated by the absorption curve ($\alpha$), the coefficient of absorption $\alpha$ increases in a wavelength region between $\lambda_z$ and $\lambda_b$. However real values of $\lambda_a$ and $\lambda_b$ and the height at the peak of the coefficient of absorption a between these wavelengths are different for every sample material. Further, the number of wavelength regions in which the coefficient of absorption $\alpha$ increases, is not necessarily restricted to 1, but there may be a plurality of such regions, depending on the sample material. On the other hand, although the coefficient of scattering s is a relatively great value, variations in the coefficient with respect to variations in the wavelength are relatively small so that the curve (s) in the whole varies only slowly.

FIG. 2B shows a curve representing the derivative by wavelength of the curve ($\alpha+s$) indicated in FIG. 2A. The value varies significantly in the wavelength region between $\lambda_a$ and $\lambda_b$. This variation is principally due to the variation in the derivative of the curve ($\alpha$) indicated in FIG. 2A. On the contrary, outside of the wavelength region between $\lambda_a$ and $\lambda_b$ the curve has an almost constant value, which depends on the derivative of the curve (s) indicated in FIG. 2A. FIG. 2C shows a curve representing the relation between the coefficient of absorption a and the derivative by wavelength thereof.

Next, returning to FIG. 1, measurement of light transmitted by the sample 18 and signal processing therefor will be explained. The light beam 36 transmitted by the sample 18 is collected by a condenser lens 37 and light 38 thus collected is separated by a dichroic mirror 39 with respect to the wavelength. Light beams thus separated with respect to the wavelength are injected in photodetectors 40 and 46, respectively. The dichroic mirror 39 is a reflecting mirror for separating the incident beam with respect to the wavelength into a transmitted light beam in the wavelength region between $\lambda_1$ and $\lambda_1+\Delta\lambda_1$ and a transmitted light beam in the wavelength region between $\lambda_2$ and $\lambda_2+\Delta\lambda_2$.

It is so adjusted that the transmitted light beam in the wavelength region between $\lambda_1$ and $\lambda_1+\Delta\lambda_1$ is injected in the photodetector 40. Since the laser diodes 13 and 21 are repeatedly alternately activated with a period $\omega_1$ of the clock signal coming from the clock signal generating circuit 11, the transmitted light beam of wavelength $\omega_1$ and the transmitted light beam of wavelength $\lambda_1+\Delta\lambda_1$ are injected alternately in the photodetector 40. In the case where the coefficients of transmission in the sample 18 are equal to each other for the wavelength $\lambda_1$ and the wavelength $\lambda_1+\Delta\lambda_1$, since the transmitted light intensities are equal to each other for the wavelength $\lambda_1$ and the wavelength $\lambda_1+\Delta\lambda_1$, the output of the photodetector 40 has only a DC component. In the case where the coefficients of transmission in the sample 18 are different from each other for the wavelength $\lambda_1$ and the wavelength $\lambda_1+\Delta\lambda_1$, since the transmitted light intensities are different from each other for the wavelength $\lambda_1$ and the wavelength $\lambda_1+\Delta\lambda_1$, the output of the photodetector 40 includes an AC component of period $\omega_1$. The magnitude of the amplitude of this AC component is proportional to a difference $\Delta I_{\lambda 1}$ between the transmitted light intensities for the wavelength $\lambda_1$ and the wavelength $\lambda_1+\Delta\lambda_1$.

Filter circuits 41 and 44 are connected with the photodetector 40 on the output side. The former circuit 41 makes the AC component of period $\omega_1$ pass through, and the latter circuit 44 makes the DC component pass through. In the stage succeeding the filter circuit 41 there is disposed a smoothing circuit 42 for smoothing the AC component, which has been made selectively to pass through. A calculating circuit 43 disposed further thereafter is used for calculating the value of $S_1$, which is expressed by a following formula, using the output of the smoothing circuit 42 and the output of the filter circuit 44:

$$S_1 = \frac{C}{I_{\lambda 1}} \cdot \frac{\Delta I_{\lambda 1}}{\Delta \lambda_1} \qquad (4)$$

where C is a coefficient determined by characteristics of the equipment.

On the other hand, the transmitted light beam of wavelength $\lambda_2$ and the transmitted light beam of wavelength $\lambda_2+\Delta\lambda_2$ are injected in the photodetector 46. Similarly to the case of the photodetector 40 described above, filter circuits 47 and 50 as well as a smoothing circuit 48 are disposed on the output side of the photodetector 46. Further the value of $S_2$, which is expressed by a following formula, is calculated by means of a calculating circuit 49:

$$S_2 = \frac{C}{I_{\lambda 2}} \cdot \frac{\Delta I_{\lambda 2}}{\Delta \lambda_2} \qquad (5)$$

When the wavelength $\lambda_1$ is set at a wavelength, at which the derivation of the coefficient of absorption $\alpha$ has a great value, within the wavelength region between $\lambda_a$ and $\lambda_b$ and the wavelength $\lambda_2$ is set outside of the region between $\lambda_a$ and $\lambda_b$, from FIG. 2B it can be understood that $S_1$ represents $$\left( \frac{\partial \alpha}{\partial \lambda} + \frac{\partial s}{\partial \lambda} \right) \cdot d$$

and $S_2$ represents $$\frac{\partial s}{\partial \lambda} \cdot d.$$

Consequently the derivative by wavelength $(\partial \alpha/\partial \lambda) \cdot d$ of the coefficient of absorption can be obtained as the difference S by forming the difference between $S_1$ and $S_2$ as follows:

$$S = S_1 - S_2 = \frac{\partial \alpha}{\partial \lambda} \cdot d \qquad (6)$$

A calculating circuit 45 calculates the value of the difference $S = S_1 - S_2 = (\partial \alpha/\partial \lambda) \cdot d$ between the values $S_1$ and $S_2$ described above. Further, another calculating circuit 51 transforms the output value S of the calculating circuit 45 into a value of the absorption coefficient $\alpha$ according to the relation between the absorption coefficient $\alpha$ and the difference S, as indicated in FIG. 2C, which separately has been obtained experimentally. In this way, it is possible to obtain the coefficient of absorption $\alpha$ of the light absorbing substance contained in the sample 18 with a high precision, while removing influences of light scattering.

EMBODIMENT 1

The present embodiment relates to a method and an apparatus for measuring the light absorption by hemoglobin in blood. Since the hemoglobin in blood is contained in the red blood cells, when they are irradiated with light, it is reflected at the surface of the blood cells to give rise to scattered light. Since this scattered light acts as significant noise light, heretofore it was not possible to measure directly the light absorbing characteristics of hemoglobin existing within the red blood cells. Usually red blood cells were destroyed so that hemoglobin contained therein was eluted and thereafter measurement of the coefficient of light absorption was effected, using this eluted hemoglobin.

FIG. 3 indicates an aspect of variations in light absorption characteristics, when hemoglobin in blood is oxygenated and when it is deoxygenated. In the figure, the curve designated by $HbO_2$ indicates the light absorption characteristics when the hemoglobin is oxygenated and the curve designated by Hb indicates them when the hemoglobin is deoxygenated. Concerning these characteristics, there is a report by Van Aassendelft, entitled "Spectrophotometry of Hemoglobin Derivatives" (C. C. Thomas, Springfield, Ill. 1970). According to these absorption characteristics, a curve representing the coefficient of absorption has double peaks when hemoglobin is perfectly oxygenated, while it has a single peak when hemoglobin is perfectly deoxygenated. As deoxygenation advances from the state where hemoglobin is perfectly oxygenated, the characteristics are varied gradually from the double peak characteristics to the single peak characteristics.

Paying attention to variations in the inclination of the characteristic curve produced at that time, in a wavelength region from about 540 nm to about 560 nm, a significant variation takes place from a negative inclination at the oxygenation to a positive inclination at the deoxygenation. On the contrary, in a wavelength region from about 560 nm to 580 nm, a significant variation takes place from a positive inclination at the oxygenation to a negative inclination at the deoxygenation. The present embodiment attempts to measure light absorption by hemoglobin in blood, using these variations.

Figure 4:
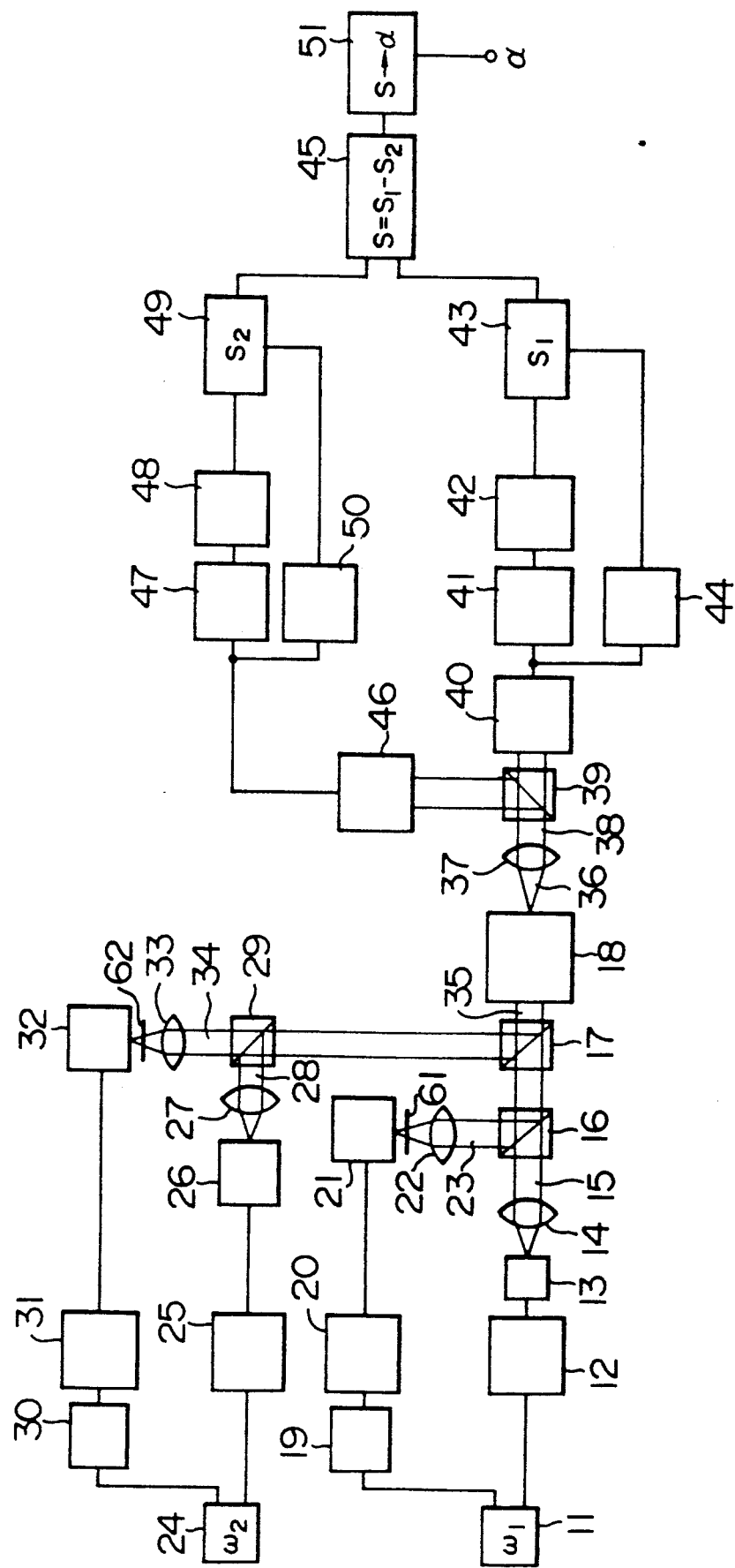
FIG. 4 is a block diagram indicating the construction of an apparatus which is an embodiment of the present invention.

FIG. 4 indicates the construction of the equipment used in the present embodiment. The construction of this equipment is basically the construction of the equipment indicated in FIG. 1, to which attenuation filters 61 and 62 are added.

In the present embodiment, elements having wavelengths of 570 nm, 572 nm, 670 nm and 672 nm are used for the laser diodes 13, 21, 26 and 32, respectively. For the group of the laser diodes 13 and 21 as well as for the groups of the laser diodes 26 and 32, elements having the same laser characteristics are used for every group. The difference of 2 nm between the wavelengths of the two elements is produced by varying the laser power for the two elements. This utilizes the phenomenon that even for elements having completely identical laser characteristics, when the laser powers thereof are different, since heat production at the junction portions thereof are different, temperatures at the junction portions are also different and that therefore, since energy band gaps of semiconductor crystals therefor are different, the wavelengths of laser are different.

As described above, since in the present embodiment, two elements having the same laser characteristics are used for every group of laser diodes and the necessary difference in the wavelength of a laser is obtained for every group by using different laser outputs for the two elements, it is a matter of course that a difference is produced between the output powers of the laser diodes for every group. The attenuation filters newly added in the present embodiment are disposed for equalizing powers of the laser light beams 23 and 34 outputted by the laser diodes 21 and 32 to powers of the laser light beams 15 and 28 outputted by the laser diodes 13 and 26, respectively.

The frequencies of the clock signals outputted by the clock signal generating circuits 11 and 24 for controlling the duty cycles of laser light pulses of the laser diodes are 1 MHz and 1.5 MHz, respectively. The dichroic mirrors 17 and 39 are mirrors using thin multilayers for reflection layers, provided with characteristics by which light beams of wavelengths 570 nm and 572 nm are made to pass through, and light beams of wavelengths 670 nm and 672 nm are reflected, respectively. Photomultipliers are used for the photodetectors 40 and 46. The filter circuits 41 and 47 are band pass filters, which make AC components of 1 MHz and 1.5 MHz pass through, respectively.

Now the operation of the equipment used in the present embodiment will be explained. At first, when the clock signal of 1 MHz is generated by the clock signal generating circuit 11, this clock signal is transmitted directly to the laser diode power supply 12, while this clock signal is transmitted to the laser diode power supply 20 after having been inverted by the inversion circuit 19. For this reason, the timing of the activation of the laser diode 21, whose activation is controlled by the laser diode power supply 20, and that of the laser diode 13, whose activation is controlled by the laser diode power supply 12, are exactly opposite to each other. That is, the laser diodes 13 and 21 are activated alternately. The intensity of the laser light beam outputted by the laser diode 21 is lowered by the attenuation filter 61 and the laser light beams 15 and 23 are adjusted in this way so as to have the same intensity. The laser light beams outputted by the laser diodes 13 and 21 are collimated by the collimator lenses 14 and 22 to be transformed into the parallel light beams 15 and 23, respectively. These laser light beams 15 and 23 pass through the dichroic mirror 17 after having been superposed on each other on a common optical path by means of the polarizer 16, and the sample 18 is irradiated therewith.

On the other hand, the clock signal of 1.5 MHz is generated by the clock signal generating circuit 24. This clock signal is transmitted directly to the laser diode power supply 25, while it is transmitted to the laser diode power supply 31 after having been inverted by the inversion circuit 30. Consequently the laser diodes 26 and 32 are activated alternately at a frequency of 1.5 MHz. The laser light beam outputted by the laser diode 32 is attenuated by the attenuation filter 62. The laser light beams 28 and 34 are adjusted so that the intensities thereof are equal to each other. The laser light beams outputted by the laser diodes 26 and 32 are collimated by the collimator lenses 27 and 33 to be transformed into the parallel light beams 28 and 34, respectively. These laser light beams 28 and 34 are superposed on each other on a common optical path by the polarizer 29 and further reflected by the dichroic mirror 17 so as to be superposed on the light path 35 of the laser light beams 15 and 23 described previously. Thereafter the sample 18 is irradiated therewith.

The laser light beams, with which the sample 18 is irradiated, are partly transmitted by the sample, while being subjected to attenuation due to absorption and scattering in the sample. The light 36 transmitted by the sample is collected by the condenser lens 37. Then the light 38 thus collected is divided into two light beams by the dichroic mirror 39, one of which includes light beams of wavelengths 570 nm and 572 nm injected in the photodetector 40, while the other includes light beams of wavelengths 670 nm and 672 nm injected in the photodetector 46.

Here, as can be understood from the characteristic curves indicated in FIG. 3, the laser light beams of wavelengths of 570 nm and 572 nm injected in the photodetector 40 are in a wavelength region where the coefficient of absorption is varied remarkably by the fact that the degree of oxygenation of hemoglobin is varied.

Since the intensities of the laser light beams of wavelengths 570 nm and 572 nm injected in the sample are equal to each other, the intensities of the laser light beams of wavelengths 570 nm and 572 nm transmitted by the sample reflect substantially the attenuation due to light absorption in the sample. In the case where light absorptions in the sample for the two wavelengths stated above are equal to each other, the intensities of the laser light beams of wavelengths 570 nm and 572 nm transmitted by the sample are also equal to each other. Therefore the output of the photodetector 40 includes only a DC component.

However, in the case where light absorptions in the sample for the two wavelengths stated above are different from each other, a difference in the intensity between the transmitted light beams of wavelengths 570 nm and 572 nm is produced. Therefore an AC component of frequency of 1 MHz having an amplitude proportional to this difference in the intensity $\Delta I_{\lambda 1}$ is included in the output of the photodetector 40. The filter circuit 44 extracts only the DC component from the output of the photodetector 40, while the filter circuit 41 extracts only the AC component of frequency of 1 MHz therefrom. The AC component extracted by the filter circuit 41 is converted into a DC signal by the smoothing circuit 42. The calculating circuit 43 divides the output of the smoothing circuit 42 by the output of the filter circuit 44 to obtain the $S_1$ value given by Eq. (4) $[S_1 = (C/I_{\lambda 1})(\Delta I_{\lambda 1}/\Delta \lambda_1)]$.

On the other hand, the laser light beams of wavelengths 670 nm and 672 nm are injected in the photodetector 46. Since there is no absorption peak due to hemoglobin in this wavelength region, attenuation of the transmitted light is produced almost by light scattering. The photodetector 46 transforms the intensity of injected light into an electric signal to output it. This output signal is separated into the DC component and the AC component of frequency of 1.5 MHz by means of the filter circuits 50 and 47, respectively. The AC component of frequency 1.5 MHz is further converted into a DC signal by means of the smoothing circuit 48.

The calculating circuit 49 divides the output of the smoothing circuit 48 by the output of the filter circuit 50 to obtain the $S_2$ value given by Eq. (5) $[S_2 = (C/I_{\lambda 2})(\Delta I_{\lambda 2}/\Delta \lambda_2)]$.

Then the calculating circuit 45 calculates the difference value S between the $S_1$ value and the $S_2$ value. As the result, as can be understood from Eq. (6), it is possible to obtain a value which is proportional to the inclination of the coefficient of absorption $\alpha$ of hemoglobin. Then the coefficient of absorption $\alpha$ can be obtained from the S value described above by means of the calculating circuit 51 on the basis of the relation between the S value and the coefficient of absorption $\alpha$ as indicated in FIG. 2C.

However, since the absolute value of $\Delta I$ is measured by the equipment used in the present embodiment, it cannot be judged automatically whether the derivative by wavelength of the coefficient $\alpha$ is positive or negative. In order to judge whether the derivative by wavelength of the coefficient of absorption $\alpha$ is positive or negative, it is necessary to effect the measurement, while clearly distinguishing cases where the degree of the oxygenation of hemoglobin is great from cases where it is small.

EMBODIMENT 2

The present embodiment relates to a method and an apparatus for measuring the light absorption by hemoglobin, similarly to preceding EMBODIMENT 1. In EMBODIMENT 1, since it was not possible to judge whether the derivative by wavelength of the coefficient of absorption was positive or negative, it was necessary to judge the measurement, while distinguishing cases where the degree of the oxygenation of hemoglobin was great from cases where it was small.

In the present embodiment, regardless of the sign, positive or negative, of the derivative by wavelength, the coefficient of absorption can be measured with a high precision.

Figure 5:
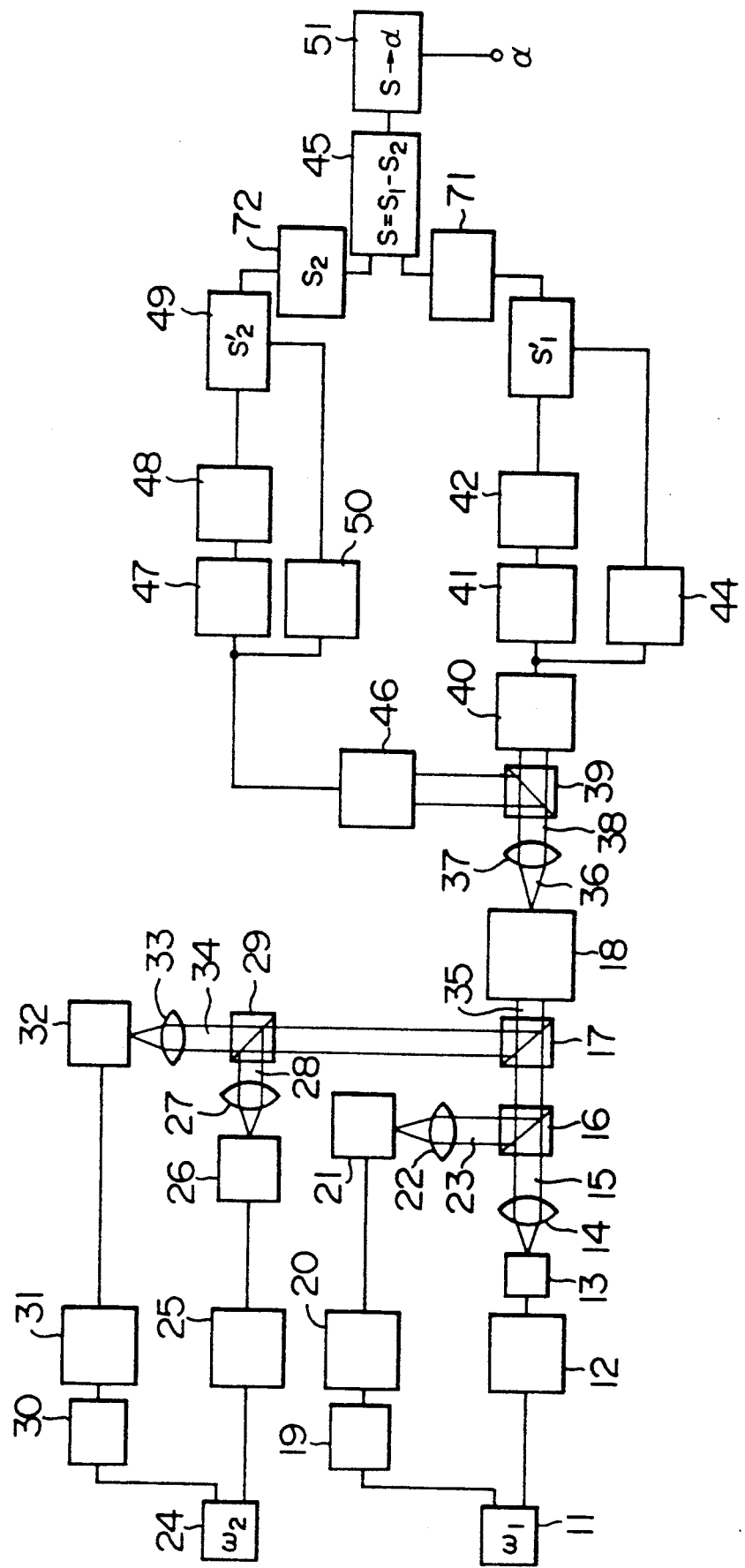
FIG. 5 is a block diagram indicating the construction of an apparatus which is another embodiment of the present invention.

FIG. 5 indicates the construction of the equipment used in the present embodiment. The difference thereof from the construction of the equipment used in EMBODIMENT 1 consists in that the attenuation filters 61 and 62 are removed from the construction of the equipment used in EMBODIMENT 1 and subtracters 71 and 72 as well as calculating devices 43 and 49 are disposed in the succeeding stage, respectively, in lieu thereof.

In the present embodiment, since the attenuation filters described previously are not used, the laser light beams 15 and 23 themselves injected in the sample are different in intensity from each other. Now it is supposed that the intensity of the incident laser light beam 23 of wavelength 572 nm is m times as high as the intensity of the incident laser light beam 15. Denoting the intensities of the transmitted light beams of wavelengths 570 nm and 572 nm, when it is supposed that the intensity of the incident laser light beam of wavelength 572 nm is equal to the intensity of the incident laser light beam of wavelength 570 nm, by $I_{570}$ and $I_{572}$, respectively, when the intensity of the incident laser light beam of wavelength 572 nm is m times as high as the intensity of the incident laser light beam of wavelength 570 nm, the intensity of the transmitted light beam of wavelength 572 nm is m times as high as $I_{572}$. The present embodiment corresponds to the case of the latter.

In order to make the explanation of the present embodiment more understandable, here it is supposed that the transmitted light of wavelength 572 nm (intensity:

$m \cdot I_{572}$) is divided into 2 components A and B. The intensity of the component A is denoted by $I_{572}$ and the intensity of the component B by $(m-1)I_{572}$.

In the case where it is considered that the transmitted light of wavelength 570 nm (intensity: $I_{570}$) is combined only with the component A of the transmitted light of wavelength 572 nm (intensity: $I_{572}$), the variation in the intensity of the transmitted light can be thought to be identical to that described in EMBODIMENT 1. In the present embodiment, since the B component of the transmitted light is added thereto, the variation in the intensity of the transmitted light as a whole $\Delta I_T$ can be expressed by the following expression:

$$\Delta I_T = (I_{572} - I_{570}) + (m-1)I_{572} = \Delta I_{\lambda 1} + (m-1)I_{572} \quad (7)$$

Further, a following expression can be obtained from this Eq. (7):

$$\begin{aligned} S_1' &= \Delta I_T/(\Delta \lambda_1 \times I_{572}) \\ &= \Delta I_{\lambda 1}/(\Delta \lambda_1 \times I_{572}) + (m-1)/\Delta \lambda_1 \\ &= \left(\frac{\partial \alpha_{\lambda 1}}{\partial \lambda_1} + \frac{\partial s_{\lambda 1}}{\partial \lambda_1}\right) \cdot d + (m-1)/\Delta \lambda_1 \\ &= S_1 + (m-1)/\Delta \lambda_1 \end{aligned} \quad (8)$$

In the present embodiment the $S_1'$ value calculated by the calculating device 43 has a content expressed by Eq. (8). Consequently the $S_1$ value $[=(\partial \alpha_{\lambda 1}/\partial \lambda_1 + \partial s_{\lambda 1}/\partial \lambda_1) \cdot d]$ can be obtained by subtracting the value of $(m-1)/\Delta \lambda_1$ from this $S_1'$ value by means of the subtracter 71.

Further the value $S_2'$ calculated by the calculating device 49 has similarly a content as expressed by the following expression, where n represents the ratio of the intensity of the incident laser light beams 34 of wavelength 672 nm to the intensity of the incident laser light beam 28:

$$\begin{aligned} S_2' &= \Delta I_T/(\Delta \lambda_2 \times I_{672}) \\ &= \Delta I_{\lambda 2}/(\Delta \lambda_2 \times I_{672}) + (n-1)/\Delta \lambda_2 \\ &= \left(\frac{\partial \alpha_{\lambda 2}}{\partial \lambda_2} + \frac{\partial s_{\lambda 2}}{\partial \lambda_2}\right) \cdot d + (n-1)/\Delta \lambda_2 \\ &= S_2 + (n-1)/\Delta \lambda_2 \end{aligned} \quad (9)$$

Also in this case, the $S_2$ value $$\left[ = \left(\frac{\partial \alpha_{\lambda 2}}{\partial \lambda_2} + \frac{\partial s_{\lambda 2}}{\partial \lambda_2}\right) \cdot d \right]$$

can be obtained by subtracting the value of $(n-1)\Delta \lambda_2$ from the $S_2'$ value by means of the subtracter 72. Thereafter, similarly to EMBODIMENT 1, the S value corresponding to the derivative by wavelength of the absorption coefficient $\alpha$ can be obtained by subtracting $S_2$ from $S_1$ by means of the calculating circuit 45. Furthermore, the value of the coefficient absorption is obtained from this S value by means of the calculating device 51.

As clearly seen from the above description in detail, according to the present invention, it is possible to measure the coefficient of light absorption of a light absorbing substance in a light scattering material with a high precision.

We claim:

1. A method of measuring absorptance of a light scattering material, comprising the steps of:
   irradiating a light scattering material alternately with first and second laser light beams respectively having slightly different wavelengths from each other which are within a wavelength region that is selectively absorbed by said light scattering material;
   measuring a first ratio of a ratio of an intensity difference between the first and second laser light beams transmitted through said light scattering material to a wavelength difference between the first and second laser light beams, to the intensity of said first laser light beam transmitted through said light scattering material;
   irradiating said light scattering material alternately with third and fourth laser light beams respectively having slightly different wavelengths from each other which are outside of the wavelength region that is selectively absorbed by the light scattering material;
   measuring a second ratio of a ratio of an intensity difference between the third and fourth laser light beams transmitted through said light scattering material to a wavelength difference between the third and fourth laser light beams, to the intensity of said third laser light beam transmitted through said light scattering material;
   determining a difference between said first ratio and said second ratio; and
   obtaining the absorptance of said light scattering material corresponding to said difference between the first and second ratios.

2. An apparatus for measuring absorptance of a light scattering material, comprising:
   means for irradiating a light scattering material alternately with first and second laser light beams respectively having slightly different wavelengths from each other which are within a wavelength region that is selectively absorbed by said light scattering material;
   means for measuring a first intensity difference between the first and second laser light beams transmitted through said light scattering material;
   means for calculating a first ratio of a ratio of said first intensity difference to a wavelength difference between the first and second laser light beams, to the intensity of said laser light beam transmitted through said light scattering material;
   means for irradiating said light scattering material alternately with third and fourth laser light beams respectively having slightly different wavelengths from each other which are outside of the wavelength region selectively absorbed by the light scattering material;
   means for measuring a second intensity difference between the third and fourth laser light beams transmitted through said light scattering material;
   means for calculating a second ratio of a ratio of said second intensity difference between the third and fourth laser light beams transmitted through said light scattering material to a wavelength difference between the third and fourth laser light beams, to the intensity of said third laser light beam transmitted through said light scattering material;
   means for determining a difference between said first ratio and said second ratio; and means for obtaining the absorptance of said light scattering material corresponding to said difference between the first and second ratios.

3. An apparatus for measuring absorptance of a light scattering material according to claim 2, wherein the first to fourth laser light beams, with which said light scattering material is irradiated, are provided by respective first to fourth semiconductor laser devices.

4. An apparatus for measuring absorptance of a light scattering material according to claim 3, wherein the first and second semiconductor laser devices have oscillation characteristics identical to each other, and the wavelengths of the outputted laser light beams can be varied by varying laser powers thereof.

5. An apparatus for measuring absorptance of a light scattering material according to claim 3, wherein the third and fourth semiconductor laser devices have oscillation characteristics identical to each other, and the wavelength of the outputted laser light beams can be varied by varying laser power thereof.

6. An apparatus for measuring absorptance of a light scattering material according to claim 4, wherein said slight wavelength difference between said first and said second laser light beams is produced by a difference between said laser powers of said first and said second semiconductor laser devices.

7. An apparatus for measuring absorptance of a light scattering material according to claim 5, wherein said slight wavelength difference between said third and said fourth laser light beams is produced by a difference between said laser powers of said third and fourth semiconductor laser devices.

8. An apparatus for measuring absorptance of a light scattering material according to claim 6, further comprising an attenuation filter for attenuating the intensity of the laser light beam outputted by the one of said first and said second semiconductor laser devices having the higher laser power to the intensity of the other of the first and second laser light beams in order to equalize the intensities of said first and said second laser light beams projected to said sample with each other.

9. An apparatus for measuring absorptance of a light scattering material according to claim 7, further comprising an attenuation filter for attenuating the intensity of the laser light beam outputted by the one of said third and said fourth semiconductor laser devices having the higher laser power to the intensity of the other of said third and fourth laser light beams in order to equalize the intensities of said third and fourth laser light beams projected to said sample with each other.

10. An apparatus for measuring absorptance of a light scattering material according to claim 6, wherein the intensities of said first and said second laser light beams projected to said sample are different from each other, and said means for calculating said first ratio includes means for correcting measurement errors due to said intensity difference between the first and the second laser light beam projected to said sample.

11. An apparatus for measuring absorptance of a light scattering material according to claim 7, wherein the intensities of said third and said fourth laser light beams projected to said sample are different from each other, and said means for calculating said second ratio includes means for correcting measurement errors due to said intensity difference between the third and the fourth laser light beam projected to said sample.

12. A method of measuring absorptance of a light scattering material, comprising the steps of:
irradiating a light scattering material with first and second laser light beams respectively having different wavelengths from each other which are within a wavelength region that is selectively absorbed by said light scattering material;
irradiating said light scattering material with third and fourth laser light beams respectively having different wavelengths from each other which are outside of the wavelength region that is selectively absorbed by the light scattering material; and
obtaining the absorptance of said light scattering material by measuring the transmittance of said light scattering material for each of the first, second, third and fourth laser light beams.

13. An apparatus for measuring absorptance of alight scattering material, comprising:
means for irradiating a light scattering material with first and second laser light beams respectively having different wavelengths from each other which are within a wavelength region that is selectively absorbed by said light scattering material;
means for measuring a first intensity difference between the first and second laser light beams transmitted through said light scattering material;
means for irradiating said light scattering material with third and fourth laser light beams respectively having different wavelengths from each other which are outside of the wavelength region selectively absorbed by said light scattering material;
means for measuring a second intensity difference between the third and fourth laser light beams transmitted through said light scattering material; and
means for obtaining the absorptance of said light scattering material in accordance with the first and second intensity difference.

14. An apparatus for measuring absorptance of a light scattering material, comprising:
means for irradiating a light scattering material with first and second laser light beams respectively having different wavelengths from each other which are within a wavelength region that is selectively absorbed by said light scattering material;
means for irradiating said light scattering material with third and fourth laser light beams respectively having different wavelengths from each other which are outside of the wavelength region selectively absorbed by said light scattering material; and
means for measuring the transmittance of said light scattering material for each of the first, second, third and fourth laser light beams to obtain the absorptance of said light scattering material.

* * * * *